United States Patent [19]

Boller et al.

[11] 4,364,838

[45] Dec. 21, 1982

[54] LIQUID CRYSTAL MIXTURES

[75] Inventors: Arthur Boller, Binningen; Alfred Germann, Basel; Martin Schadt, Seltisberg; Alois Villiger, Basel, all of Switzerland

[73] Assignee: Hoffmann-La Roche Inc., Nutley, N.J.

[21] Appl. No.: 205,181

[22] Filed: Nov. 10, 1980

Related U.S. Application Data

[63] Continuation-in-part of Ser. No. 131,320, Mar. 18, 1980, abandoned.

[30] Foreign Application Priority Data

Nov. 14, 1979 [CH] Switzerland .................. 10154/79
Jun. 17, 1980 [CH] Switzerland .................. 4651/80
Sep. 9, 1980 [CH] Switzerland .................. 6767/80

[51] Int. Cl.$^3$ .......................... C09K 3/34; G02F 1/13
[52] U.S. Cl. ........................ 252/299.61; 252/299.63; 350/350 R
[58] Field of Search ................ 252/299.61, 299.63; 350/350 R

[56] References Cited

U.S. PATENT DOCUMENTS

| | | |
|---|---|---|
| 3,923,857 | 12/1975 | Boller et al. |
| 3,927,064 | 12/1975 | Boller et al. |
| 3,947,375 | 3/1976 | Gray et al. |
| 3,997,536 | 12/1976 | Boller et al. .................. 252/299.61 |
| 4,062,798 | 12/1977 | Boller et al. .................. 252/299.61 |
| 4,130,502 | 12/1978 | Eidenschink et al. |
| 4,145,114 | 3/1979 | Coates et al. |
| 4,149,413 | 4/1979 | Gray et al. |
| 4,180,475 | 12/1979 | Schadt et al. ................. 252/299.5 |
| 4,198,130 | 4/1980 | Boller et al. .................. 252/299.5 |
| 4,200,580 | 4/1980 | Hsu ................................ 252/299.61 |
| 4,203,862 | 5/1980 | Hsu . |
| 4,208,106 | 6/1980 | Oh . |
| 4,273,929 | 6/1981 | Boller et al. .................. 252/299.1 |
| 4,322,354 | 3/1982 | Sorkin ........................... 252/299.61 |

FOREIGN PATENT DOCUMENTS

| | | |
|---|---|---|
| 2815860 | 10/1978 | Fed. Rep. of Germany ... 252/299.1 |
| 2846409 | 6/1979 | Fed. Rep. of Germany ......... 252/299.61 |
| 2854310 | 6/1979 | Fed. Rep. of Germany ......... 252/299.63 |
| 105701 | 5/1974 | German Democratic Rep. .................. 252/299.63 |
| 139852 | 1/1980 | German Democratic Rep. .................. 252/299.61 |
| 139867 | 1/1980 | German Democratic Rep. .................. 252/299.61 |
| 54-6884 | 1/1979 | Japan ............................. 252/299.63 |
| 54-11887 | 1/1979 | Japan ............................. 252/299.63 |
| 56-45976 | 4/1981 | Japan ............................. 252/299.61 |
| 2067586 | 7/1981 | United Kingdom ........... 252/299.67 |

OTHER PUBLICATIONS

Boller, A. et al., Mol. Cryst. Liq. Crst., vol. 42, pp. 215-231, (1977).
Demus, D., "Nonemissive Electro-Optic Displays", Kmetz, A. R. et al., Eds., Plenum Press, N.Y., pp. 83-119, (1976).
Demus et al., Chem. Abst. 90:38956n, (1979), Boller et al.
Boller et al., Derwent 76825A/43, (1977).
Constant et al., Photostable Anthraquinone Pleochroic Dyes, Presented at 7th Int. L. C. Conf., Bordeaux, France, (Aug. 1978).
Cox, R. J., Mol. Cryst. Liq. Cryst., vol. 55, Liquid Crystal Guest-Host Systems, pp. 1-32, (1979).
Demus et al., Chem. Abst. 89:129118m, (1978).
Sorkin, H., Mol. Cryst. Liq. Cryst., vol. 56, (Letters), pp. 279-281, (May, 1980).

*Primary Examiner*—Teddy S. Gron
*Attorney, Agent, or Firm*—Jon S. Saxe; Bernard S. Leon; George W. Johnston

[57] ABSTRACT

Liquid crystalline mixtures comprising trans-phenyldioxane, phenylpyrimidine and phenylbenzoate compounds which are useful in electro-optical apparatuses are disclosed.

37 Claims, No Drawings

LIQUID CRYSTAL MIXTURES

RELATED APPLICATIONS

This is a continuation-in-part of U.S. Patent Application Ser. No. 131,320 filed Mar. 18, 1980, now abandoned.

BACKGROUND OF THE INVENTION

This invention relates to liquid crystalline mixtures.

In an electric field, the molecules of liquid crystalline compounds and mixtures which possess a positive anisotropy of the dielectric constants (i.e., $\epsilon_{\parallel} > \epsilon_{\perp}$) are oriented with their longitudinal axes parallel to the field direction. $\epsilon_{\parallel}$ signifies the dielectric constant along the longitudinal axis of the molecule and $\epsilon_{\perp}$ signifies the dielectric constant perpendicular thereto.

This dielectric field effect is utilized in the interaction between the liquid crystalline molecules and guest molecules (guest-host interaction) described by J. H. Heilmeier and L. A. Zanoni [Applied Physics Letters 13, 91 (1968)]. Another application of the dielectric field effect is the electro-optical rotation cell discovered by M. Schadt and W. Helfrich [Applied Physics Letters 18, (1971)]. A further example is the Kerr cell described in Molecular Crystals and Liquid Crystals 17, 355 (1972).

The above electro-optical rotation cell includes a condenser-like structure having transparent electrode plates, the dielectric of which is formed from nematic liquid crystal material with $\epsilon_{\parallel} > \epsilon_{\perp}$. The longitudinal axes of the liquid crystal molecules are arranged in twisted or helical form between the plates in the field-less state. The twisting structure is determined by the given wall orientation of the molecules. After applying an electric potential to the condenser plates, the molecules adjust themselves with their longitudinal axes in the field direction (i.e., perpendicular to the surface of the plates), so that linear polarized light no longer rotates in the dielectric (the liquid crystal is uniaxially perpendicular to the surface of the plates). After removing the electric potential, the molecules return to their prior orientation. This reversible effect on the molecules can be used to electrically control the optical transmissivity of the condenser. To achieve an optimal transition between these two orientations, the threshold potential of the compounds or mixtures is adjusted to the driving potential of the rotation cell. The driving potential of such a "light rotation cell" is dependent on the battery potential and the control circuit used.

In a rotating cell, it is desirable to use compounds or mixtures which have low threshold and operating potentials. This is particularly important when using the rotation cells in clock displays.

We have invented liquid crystalline mixtures which advantageously possess low threshold and operational potentials.

SUMMARY

The invention relates to liquid crystalline mixtures comprising a trans-phenyl dioxane of the formula:

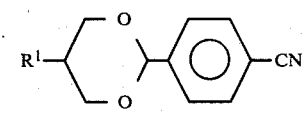

a phenylpyrimidine of the formula:

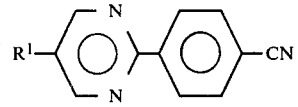

and a phenylbenzoate of the formula:

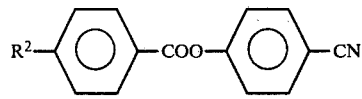

wherein $R^1$ is straight chain alkyl of 3 to 7 carbon atoms and $R^2$ is straight chain alkyl of 2 to 7 carbon atoms.

The liquid crystalline mixtures may also contain a compound of the formula:

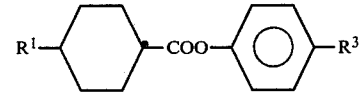

wherein at least one of rings A and B is trans-1,4-disubstituted cyclohexane and the other ring is trans-1,4-disubstituted cyclohexane or aromatic and R is straight chain alkyl, alkoxy of 1 to 10 carbon atoms or $C_2H_5—CH(CH_3)—(CH_2)_n—$, wherein n is an integer of 1 to 3; a compound of the formula:

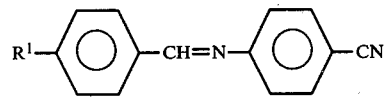

wherein $R^1$ is straight chain alkyl of 3 to 7 carbon atoms and $R^3$ is cyano or straight chain alkoxy of 1 to 3 carbon atoms, and/or a Schiffs base of the formula:

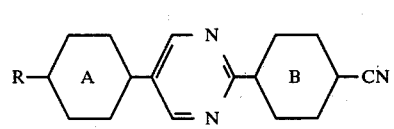

wherein $R^1$ is straight chain alkyl of 3 to 7 carbon atoms.

The inventive mixtures are useful in electro-optical apparatuses and possess especially low operation and threshold voltages as well as low viscosities.

The invention is further concerned with liquid crystal compounds, mixtures, processes, uses and apparatuses as described below.

DETAILED DESCRIPTION OF THE INVENTION

The present invention relates to liquid crystalline mixtures comprising about 10 to about 75 mol percent of one or more trans-phenyldioxanes of the formula:

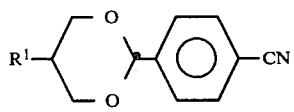

wherein $R^1$ is straight chain alkyl of 3 to 7 carbon atoms, about 5 to about 30 mol percent of one or more phenylpyrimidines of the formula:

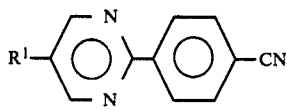 VII wherein $R^1$ is as above, and about 2 to about 20 mol percent of one or more phenylbenzoates of the formula:

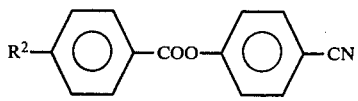 VIII wherein $R^2$ is straight chain alkyl of 2 to 7 carbon atoms.

Compounds I, VII and VIII are nematic liquid crystals and they possess a high-positive anisotropy of the dielectric constants ($\epsilon_\parallel > \epsilon_\perp$). The compounds preferably are used in mixtures with positive dielectric anisotropy.

The mixtures of the present invention possess especially low operation and threshold voltages. Moreover, the inventive mixtures have very low viscosities and correspondingly short operating times in rotation cells. Further, compounds I, VII and VIII are colorless, possess a good chemical stability and are miscible with all known nematic substances.

The invention also is concerned with the manufacture of the inventive liquid crystalline mixtures as well as their use in electro-optical apparatuses.

As used herein, "alkyl" denotes a straight chain alkyl group of 1 to 10 carbon atoms or a branched chain alkyl group of the formula $C_2H_5$—$CH(CH_3)$—$(CH_2)_n$— wherein n is an integer from 1 to 3. Exemplary straight chain alkyl groups are methyl, ethyl, propyl, butyl, pentyl, hexyl, heptyl, octyl, nonyl and decyl. "Straight chain alkoxy" have 1 to 10 carbon atoms. Exemplary straight chain alkoxy groups are methoxy, ethoxy, propyloxy, butyloxy, pentyloxy, hexyloxy, heptyloxy, octyloxy, nonyloxy and decyloxy. Aromatic means that the ring in question is the phenyl ring.

In accordance with the invention, compound I can be manufactured by:

(a) reacting a compound of the formula:

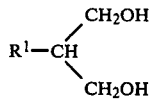 II wherein $R^1$ is as above, with an aldehyde of formula:

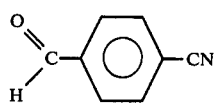 III or with an acetal of aldehyde III (compound IIIa), or (b) dehydrating a compound of the formula:

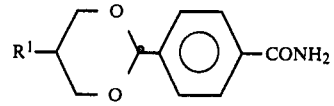 IV wherein $R^1$ is as above.

The reaction of compound II with aldehyde III can be effected by any known method for manufacturing acetals. Alternatively, compound II can be reacted with acetal IIIa by conventional procedures. Either of these two reactions (Reaction a) preferably can be carried out in an inert organic solvent with the addition of a catalytic amount of an organic or inorganic acid. Hydrocarbon compounds such as aromatic hydrocarbons (e.g., benzene, toluene, xylene and the like) are suitable solvents. Preferred acids are dry hydrogen chloride and sulphonic acids, particularly p-toluenesulphonic acid. The reaction with aldehyde III preferably is carried out at the reflux temperature of the reaction mixture, and the resulting water is separated with a water separator or a drying agent. When acetal IIIa is used as a starting material, the reaction temperature preferably is between about 50° C. and about the reflux temperature of the reaction mixture. Pressure is not critical and (Reaction a) preferably is carried out at atmospheric pressure. The resulting phenyldioxanes of formula I are obtained as cis/trans mixtures. Conventional techniques such as recrystallization can be used to separate the cis/trans components. For example, the pure trans compounds can be obtained (after removal of the acid) by recrystallization, and the mother liquors (which are enriched in cis compound) can be converted with acid again into the cis/trans equilibrium mixture and recrystallized.

Dehydration (Reaction b) can be carried out with any suitable dehydration agent, such as benzenesulphonyl chloride, N,N'-dicyclohexyl-carbodiimide and the like. Dehydration with benzenesulphonyl chloride is carried out in the presence of a base such as sodium acetate, pyridine or triethylamine. If desired, an inert organic solvent can be utilized. Dehydration with N,N'-dicyclohexyl-carbodiimide is carried out in an inert organic solvent such as a hydrocarbon (e.g., benzene). Although temperature is not critical, the dehydration usually is carried out between about 50° C. and about the reflux temperature of the reaction mixture. Pressure also is not critical and the reaction advantageously is carried out at atmospheric pressure.

Compounds II, III, IIIa, VII and VIII are known or can be manufactured from known compounds by conventional techniques.

Additionally, compound IV can be produced by the following Reaction Scheme 1 wherein $R^1$ is alkyl of 3 to 7 carbon atoms. The starting compounds and reactants shown on Reaction Scheme 1 are known or can be produced from known compounds by conventional techniques.

REACTION SCHEME 1

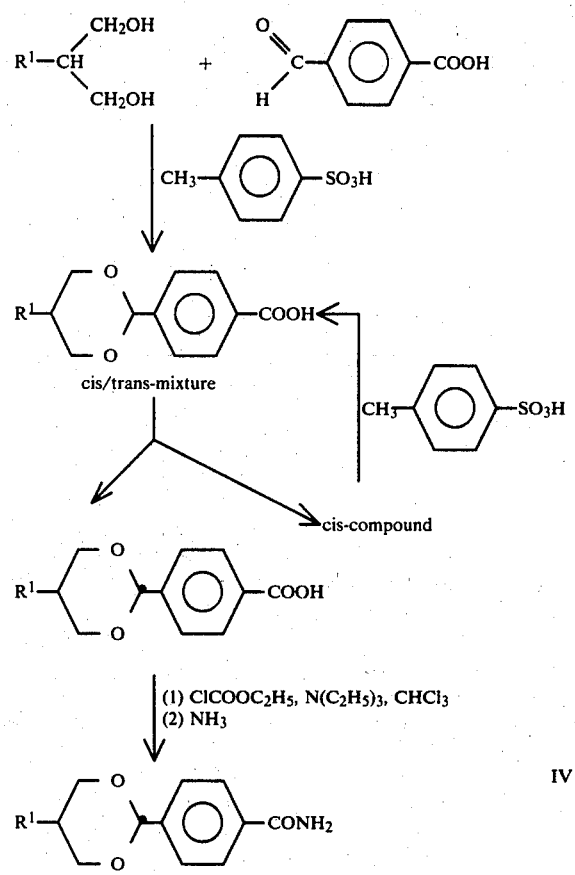

cis/trans-mixture

→ cis-compound (1) ClCOOC$_2$H$_5$, N(C$_2$H$_5$)$_3$, CHCl$_3$
(2) NH$_3$

IV

In addition to phenyldioxane I, phenylpyrimidines VII and phenylbenzoates VIII, the inventive mixtures can contain further liquid crystalline and/or non-liquid crystalline substances. Illustratively, such substances include Schiffs bases, azo- or azoxybenzenes, phenylbenzoates, cyclohexane carboxylic acid phenyl esters, bi- and terphenyls, phenylcyclohexanes, cinnamic acid derivatives, phenyl- and diphenylpyrimidines, tolanes, derivatives of thiobenzoic acid and of thiophenol and the like. Such substances are known to a person skilled in the art. See, e.g., German Offenlegungsschriften Nos. 2,306,738 (U.S. Pat. No. 3,927,064), 2,306,739 (U.S. Pat. No. 3,923,857), 2,429,093, 2,356,085 (U.S. Pat. No. 3,947,375), 2,636,684 (U.S. Pat. No. 4,130,502), 2,459,374 (U.S. Pat. No. 3,927,066), 2,547,737 (U.S. Pat. No. 3,997,536), 2,641,724 (U.S. Pat. No. 4,062,798), 2,708,276 (U.S. Pat. No. 4,180,475) and 2,811,001. Many of such nematic or non-nematic substances are commercially available.

In addition to compounds I, VII and VIII the inventive mixtures can also contain one or more compounds of the formula:

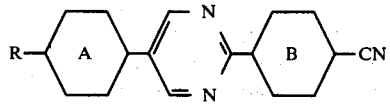

V wherein at least one of the rings A and B is trans-1,4-disubstituted cyclohexane and the other is trans-1,4-disubstituted cyclohexane or aromatic and R is straight chain alkyl of 1 to 10 carbon atoms, straight chain alkoxy of 1 to 10 carbon atoms or C$_2$H$_5$—CH(CH$_3$)—(CH$_2$)$_n$—, wherein n is an integer of 1 to 3.

Preferred inventive mixtures comprise compounds I, VII, VIII and at least one compound of formula V, wherein ring B is aromatic and R is straight chain alkyl of 2 to 7 carbon atoms.

The compounds of formula V are novel. They can be manufactured by dehydrating a compound of the formula:

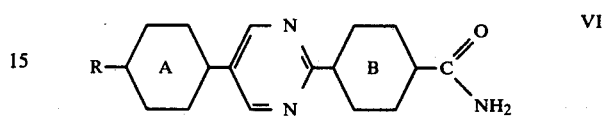

VI wherein R and rings A and B are as above.

The dehydration of compound VI can be carried out with any suitable dehydration agent such as phosphorus oxychloride, phosphorus pentoxide, thionyl chloride, acetic anhydride or, especially, benzenesulphonyl chloride and the like. Although not required, the dehydration can be effected in an inert organic solvent such as a hydrocarbon (e.g., benzene, toluene) or halogenated hydrocarbon (e.g., methylene chloride). If desired, the dehydration occurs in the presence of a base such as sodium acetate, pyridine or triethylamine. The reaction temperature preferably is between about 50° C. and about the reflux temperature of the reaction mixture. Pressure is not critical and the reaction advantageously is carried out at atmospheric pressure.

Compound VI can be produced by the following Reaction Schemes 2–4. Reaction Scheme 2 illustrates the manufacture of compound VI wherein ring A is trans 1,4-disubstituted cyclohexane, ring B is 1,4-disubstituted phenyl and R is as above (compound VIa). Reaction Scheme 3 illustrates the manufacture of compound VI wherein ring A is 1,4-disubstituted phenyl, ring B is trans-1,4-disubstituted cyclohexane and R is as above (compound VIb). Reaction Scheme 4 illustrates the manufacture of compound VI wherein rings A and B each are trans 1,4-disubstituted cyclohexane and R is as above (compound VIc).

REACTION SCHEME 2

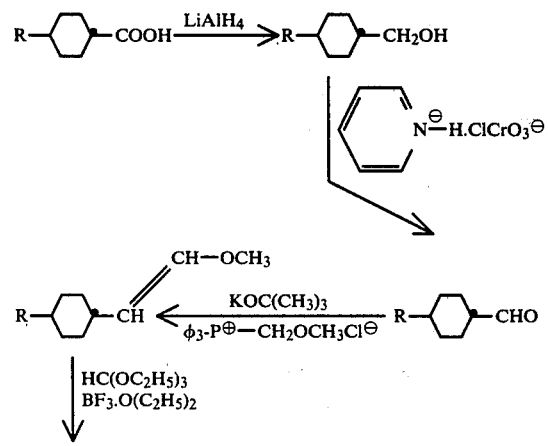

REACTION SCHEME 2

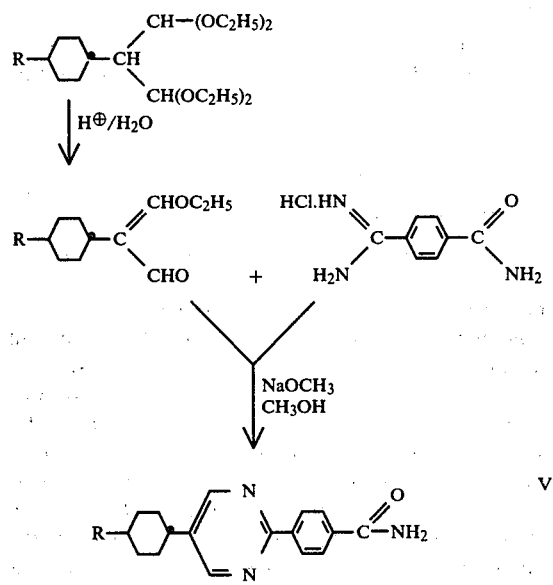

REACTION SCHEME 3

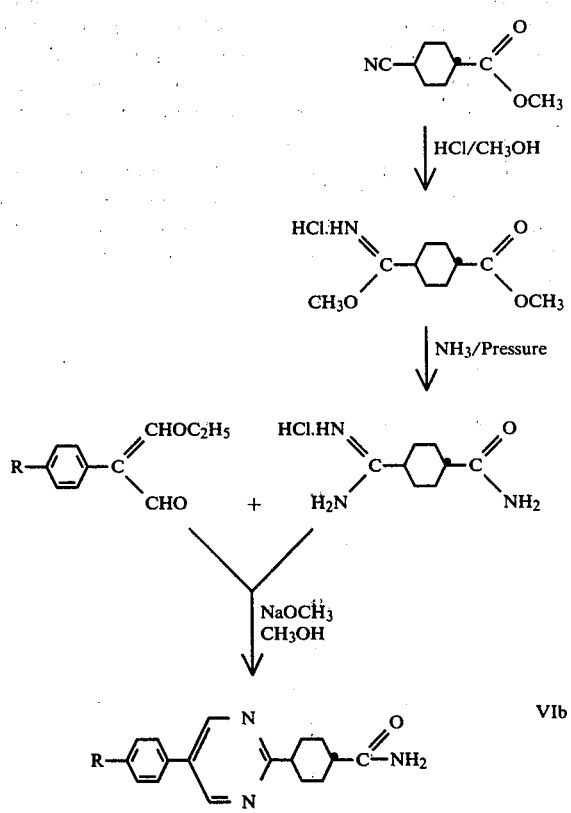

REACTION SCHEME 4

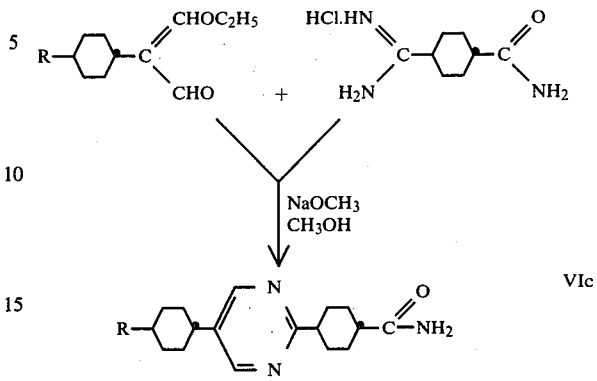

Starting acids for Reaction Scheme 2, which possess a branched side chain R can be manufactured by the process described by Gray and McDonnell in German Offenlegungsschrift 2,736,772 (U.S. Pat. No. 4,149,413) and in Mol. Cryst. Liq. Cryst. 37 189 (1976). Other starting compounds and reactants for Reaction Schemes 2–4 are known or can be produced from known compounds by standard techniques.

By the previously described method for dehydrating compound VI, compound VIa can be dehydrated to compounds V wherein ring A is trans-1,4-disubstituted cyclohexane, ring B is 1,4-disubstituted phenyl and R is as above (compound Va). Similarly, compound VIb can be dehydrated to compound V wherein ring A is 1,4-disubstituted phenyl, ring B is trans-1,4-disubstituted cyclohexane and R is as above (compound Vb). Additionally, compound VIc can be dehydrated to compound V wherein rings A and B each are trans-1,4-disubstituted cyclohexane and R is as above (compound Vc).

In another aspect of the invention, the present mixtures also can contain one or more trans-cyclohexane carboxylic acid phenyl esters of the formula:

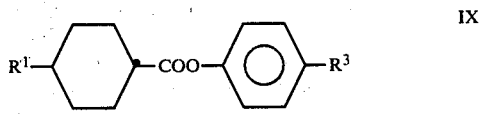

IX wherein $R^1$ is straight chain alkyl of 3 to 7 carbon atoms and $R^3$ is cyano or straight chain alkoxy of 1 to 3 carbon atoms. The inventive mixtures may also include one or more Schiffs bases of the formula:

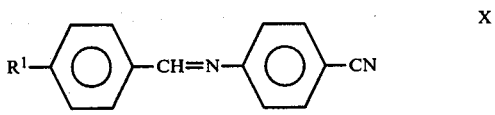

X wherein $R^1$ is straight chain alkyl of 3 to 7 carbon atoms.

Compounds IX and X are known or can be produced from known compounds by conventional techniques.

Exemplary compounds of formulas I, V and VII-X are:

p-(trans-5-propyl-m-dioxan-2-yl)benzonitrile;
p-(trans-5-butyl-m-dioxan-2-yl)benzonitrile;
p-(trans-5-pentyl-m-dioxan-2-yl)benzonitrile;

p-(trans-5-hexyl-m-dioxan-2-yl)benzonitrile;
p-(trans-5-heptyl-m-dioxan-2-yl)benzonitrile;
trans-p-[5-(4-ethylcyclohexyl)-2-pyrimidinyl]benzonitrile;
trans-p-[5-(4-pentylcyclohexyl)-2-pyrimidinyl]benzonitrile;
trans-p-[5-(4-heptylcyclohexyl)-2-pyrimidinyl]benzonitrile;
p-(5-pentyl-2-pyrimidinyl)benzonitrile;
p-(5-heptyl-2-pyrimidinyl)benzonitrile;
p-ethylbenzoic acid p'-cyanophenyl ester;
p-butylbenzoic acid p'-cyanophenyl ester;
p-pentylbenzoic acid p'-cyanophenyl ester;
p-hexylbenzoic acid p'-cyanophenyl ester;
trans-4-propylcyclohexane carboxylic acid p-cyanophenyl ester;
trans-4-butylcyclohexane carboxylic acid p-cyanophenyl ester;
trans-4-pentylcyclohexane carboxylic acid p-cyanophenyl ester;
trans-4-butylcyclohexane carboxylic acid p-(ethoxy)phenyl ester;
trans-4-pentylcyclohexane carboxylic acid p-(methoxy)phenyl ester;
trans-4-pentylcyclohexane carboxylic acid p-(propyloxy)phenyl ester
p-[(p-propylbenzyliden)amino]benzonitrile,
p-[(p-butylbenzyliden)amino]benzonitrile,
p-[(p-hexylbenzyliden)amino]benzonitrile, The weight ratio of the components of the inventive mixtures preferably corresponds to the eutectic composition. Especially preferred concentration ranges are about 30 to about 70 mol percent for compound I, about 10 to about 25 mol percent for compound VII and about 5 to about 17 mol percent for compound VIII.

When one or more compounds of formulas V, IX and X are present in the inventive mixtures, such compounds generally constitute at least about 1 mol percent. Moreover, compound V may be present in the mixture at up to about 15 mol percent. Compounds IX and/or X may be present at up to about 30 mol percent each. Preferred concentration ranges are about 2 to about 10 mol percent for compound V, about 10 to about 30 mol percent for compound IX and about 10 to about 25 mol percent for compound X.

In an additional aspect of the invention, the present mixtures can contain dichroic coloring substances, preferably azo and azoxy coloring substances, polyenes, Schiffs bases and anthraquinone derivatives.

The inventive mixtures can have about 1 to about 4 coloring substances. In the case of anthraquinones, the amount of the coloring substance in a liquid crystalline mixture is between about 0.2 and about 3 weight percent, preferably between about 1 and about 2 weight percent. In the case of other coloring substances, the amount is between about 0.1 and about 2 weight percent, preferably between about 0.5 and about 1 weight percent.

The inventive mixtures containing compounds I, VII and VIII and, if desired, other nematic and/or non-nematic compounds (e.g., compounds V, IX and/or X) and/or one or more dichroic coloring substances can be manufactured in any known manner for producing liquid crystalline mixtures. Illustratively, the desired mixtures can be formed by heating a mixture of the desired components to a temperature barely above clearing point and then cooling the mixture.

The following non-limiting Examples 1–34 illustrate preferred inventive mixtures. Unless otherwise stated, percentages are given in mol percent and the temperatures are expressed in degrees Centigrade. $\Delta\epsilon$ signifies the relative anisotropy of the dielectric constant, $\eta$ denotes the viscosity (measured at 22° C.) and $V_{10}$ connotes the threshold potential at 0° tilt angle. The mixtures of Examples 17, 25, 33 and 34 are particularly preferred.

EXAMPLE 1

4.0% p-butylbenzoic acid p'-cyanophenyl ester,
5.0% p-(5-pentyl-2-pyrimidinyl)benzonitrile,
8.0% p-(5-heptyl-2-pyrimidinyl)benzonitrile,
16.0% trans-4-butylcyclohexane carboxylic acid p-(ethoxy)phenyl ester,
15.0% trans-4-pentylcyclohexane carboxylic acid p-(methoxy)phenyl ester,
12.0% trans-p-[5-(4-heptylcyclohexyl)-2-pyrimidinyl]benzonitrile,
20.0% p-(trans-5-butyl-m-dioxan-2-yl)benzonitrile,
11.0% p-(trans-5-pentyl-m-dioxan-2-yl)benzonitrile,
9.0% p-(trans-5-heptyl-m-dioxan-2-yl)benzonitrile,
m.p. $<0°$; cl.p.73°; $\Delta\epsilon=14.72$; $\eta=45$ cp; $V_{10}=1.34$ V.

EXAMPLE 2

6.0% p-butylbenzoic acid p'-cyanophenyl ester,
7.0% p-(5-pentyl-2-pyrimidinyl)benzonitrile,
13.0% p-(5-heptyl-2-pyrimidinyl)benzonitrile,
14.0% trans-4-butylcyclohexane carboxylic acid p-cyanophenyl ester,
12.0% trans-4-pentylcyclohexane carboxylic acid p-cyanophenyl ester,
12.0% trans-p-[5-(4-ethylcyclohexyl)-2-pyrimidinyl]benzonitrile,
20.0% p-(trans-5-propyl-m-dioxan-2-yl)benzonitrile,
16.0% p-(trans-5-pentyl-m-dioxan-2-yl)benzonitrile,
m.p. $<0°$; cl.p. 70°; $\eta=60$ cp; $V_{10}=1.26$ V.

EXAMPLE 3

6.0% p-butylbenzoic acid p'-cyanophenyl ester,
7.0% p-(5-pentyl-2-pyrimidinyl)benzonitrile,
13.0% p-(5-heptyl-2-pyrimidinyl)benzonitrile,
14.0% trans-4-propylcyclohexane carboxylic acid p-cyanophenyl ester,
12.0% trans-4-pentylcyclohexane carboxylic acid p-cyanophenyl ester,
12.0% trans-p-[5-(4-ethylcyclohexyl)-2-pyrimidinyl]benzonitrile,
20.0% p-(trans-5-propyl-m-dioxan-2-yl)benzonitrile,
16.0% p-(trans-5-pentyl-m-dioxan-2-yl)benzonitrile,
m.p. $<0°$; cl.p. 71°; $\Delta\epsilon=20.00$; $\eta=57$ cp; $V_{10}=1.68$ V.

EXAMPLE 4

8.0% p-butylbenzoic acid p'-cyanophenyl ester,
8.0% p-(5-pentyl-2-pyrimidinyl)benzonitrile,
15.0% p-(5-heptyl-2-pyrimidinyl)benzonitrile,
13.0% trans-p-[5-(4-ethylcyclohexyl)-2-pyrimidinyl]benzonitrile,
23.0% p-(trans-5-propyl-m-dioxan-2-yl)benzonitrile,
18.0% p-(trans-5-pentyl-m-dioxan-2-yl)benzonitrile,
15.0% p-(trans-5-heptyl-m-dioxan-2-yl)benzonitrile,
m.p. $<0°$; cl.p. 68°; $\Delta\epsilon=22.66$; $\eta=63.7$ cp; $V_{10}=1.15$ V.

EXAMPLE 5

7.0% p-butylbenzoic acid p'-cyanophenyl ester,
7.0% p-(5-pentyl-2-pyrimidinyl)benzonitrile,
14.0% p-(5-heptyl-2-pyrimidinyl)benzonitrile,
12.0% trans-p-[5-(4-ethylcyclohexyl)-2-pyrimidinyl]-benzonitrile,
8.0% trans-p-[5-(4-pentylcyclohexyl)-2-pyrimidinyl]-benzonitrile,
21.0% p-(trans-5-propyl-m-dioxan-2-yl)benzonitrile,
17.0% p-(trans-5-pentyl-m-dioxan-2-yl)benzonitrile,
14.0% p-(trans-5-heptyl-m-dioxan-2-yl)benzonitrile,
m.p. <0°; cl.p. 82°; $\Delta\epsilon=22.62$; $\eta=72$ cp; $V_{10}=1.24$ V.

EXAMPLE 6

4.0% p-butylbenzoic acid p'-cyanophenyl ester,
4.0% p-(5-pentyl-2-pyrimidinyl)benzonitrile,
8.0% p-(5-heptyl-2-pyrimidinyl)benzonitrile,
10.0% trans-4-propylcyclohexane carboxylic acid p-cyanophenyl ester,
8.0% trans-4-pentylcyclohexane carboxylic acid p-cyanophenyl ester,
15.0% trans-4-butylcyclohexane carboxylic acid p-(ethoxy)phenyl ester,
14.0% trans-4-pentylcyclohexane carboxylic acid p-(methoxy)phenyl ester,
9.0% trans-p-[5-(4-ethylcyclohexyl)-2-pyrimidinyl]benzonitrile,
12.0% trans-p-[5-(4-heptylcyclohexyl)-2-pyrimidinyl]-benzonitrile,
16.0% p-(trans-5-propyl-m-dioxan-2-yl)benzonitrile,
m.p. <0°; cl.p. 91°; $\Delta\epsilon=14.89$; $\eta=52$ cp; $V_{10}=1.53$ V.

EXAMPLE 7

6.0% p-butylbenzoic acid p'-cyanophenyl ester,
6.5% p-(5-pentyl-2-pyrimidinyl)benzonitrile,
12.0% p-(5-heptyl-2-pyrimidinyl)benzonitrile,
13.5% trans-4-propylcyclohexane carboxylic acid p-cyanophenyl ester,
12.0% trans-4-pentylcyclohexane carboxylic acid p-cyanophenyl ester,
19.0% trans-4-pentylcyclohexane carboxylic acid p-(methoxy)phenyl ester,
12.0% trans-p-[5-(4-ethylcyclohexyl)-2-pyrimidinyl]-benzonitrile,
19.0% p-(trans-5-propyl-m-dioxan-2-yl)benzonitrile,
m.p. <0°; cl.p. 70°; $\Delta\epsilon=16.53$; $\eta=47.4$ cp; $V_{10}=1.33$ V.

EXAMPLE 8

5.5% p-butylbenzoic acid p'-cyanophenyl ester,
6.0% p-(5-pentyl-2-pyrimidinyl)benzonitrile,
11.0% p-(5-heptyl-2-pyrimidinyl)benzonitrile,
12.5% trans-4-propylcyclohexane carboxylic acid p-cyanophenyl ester,
11.0% trans-4-pentylcyclohexane carboxylic acid p-cyanophenyl ester,
25.0% trans-4-pentylcyclohexane carboxylic acid p-(propyloxy)phenyl ester,
11.0% trans-p-[5-(4-ethylcyclohexyl)-2-pyrimidinyl]-benzonitrile,
18.0% p-(trans-5-propyl-m-dioxan-2-yl)benzonitrile,
m.p. <10°; cl.p. 70°; $\Delta\epsilon=14.69$; $\eta=50.0$ cp; $V_{10}=1.38$ V.

EXAMPLE 9

5.0% p-butylbenzoic acid p'-cyanophenyl ester,
27.0% p-[(p-butylbenzyliden)amino]benzonitrile,
5.0% p-(5-pentyl-2-pyrimidinyl)benzonitrile,
10.0% p-(5-heptyl-2-pyrimidinyl)benzonitrile,
17.0% p-(trans-5-propyl-m-dioxan-2-yl)benzonitrile,
23.0% p-(trans-5-butyl-m-dioxan-2-yl)benzonitrile,
13.0% p-(trans-5-pentyl-m-dioxan-2-yl)benzonitrile,
m.p. <0°; cl.p. 48°; $\eta=63$ cp; $V_{10}=0.76$ V.

EXAMPLE 10

6.0% p-butylbenzoic acid p'-cyanophenyl ester,
12.0% p-[(p-propylbenzyliden)amino]benzonitrile,
6.0% p-(5-pentyl-2-pyrimidinyl)benzonitrile,
11.5% p-(5-heptyl-2-pyrimidinyl)benzonitrile,
7.0% trans-p-[5-(4-pentylcyclohexyl)-2-pyrimidinyl]-benzonitrile,
18.5% p-(trans-5-propyl-m-dioxan-2-yl)benzonitrile,
25.0% p-(trans-5-butyl-m-dioxan-2-yl)benzonitrile,
14.0% p-(trans-5-pentyl-m-dioxan-2-yl)benzonitrile,
m.p. <0°; cl.p. 63°; $\eta=58.6$ cp; $V_{10}=1.12$ V.

EXAMPLE 11

4.0% p-butylbenzoic acid p'-cyanophenyl ester,
7.0% p-[(p-propylbenzyliden)amino]benzonitrile,
33.0% p-[(p-hexylbenzyliden)amino]benzonitrile,
4.0% p-(5-pentyl-2-pyrimidinyl)benzonitrile,
7.0% p-(5-heptyl-2-pyrimidinyl)benzonitrile,
14.0% p-(trans-5-propyl-m-dioxan-2-yl)benzonitrile,
19.0% p-(trans-5-butyl-m-dioxan-2-yl)benzonitrile,
12.0% p-(trans-5-pentyl-m-dioxan-2-yl)benzonitrile,
m.p. <0°; cl.p. 52°; $\eta=65.4$ cp; $V_{10}=1.08$ V.

EXAMPLE 12

6.5% p-butylbenzoic acid p'-cyanophenyl ester,
7.0% p-(5-pentyl-2-pyrimidinyl)benzonitrile,
13.0% p-(5-heptyl-2-pyrimidinyl)benzonitrile,
9.0% trans-p-[5-(4-pentylcyclohexyl)-2-pyrimidinyl]-benzonitrile,
20.5% p-(trans-5-propyl-m-dioxan-2-yl)benzonitrile,
28.0% p-(trans-5-butyl-m-dioxan-2-yl)benzonitrile,
16.0% p-(trans-5-pentyl-m-dioxan-2-yl)benzonitrile,
m.p. <0°; cl.p. 64°.

EXAMPLE 13

75.0 wt.% of mixture 12+25.0 wt.% of the following mixture:
33.3% p-[(p-propylbenzyliden)amino]benzonitrile,
66.7% p-[(p-hexylbenzyliden)amino]benzonitrile,
m.p. <0°; cl.p. 64°; $\eta=65.6$ cp; $V_{10}=1.17$ V.

EXAMPLE 14

25.0% p-[(p-butylbenzyliden)amino]benzonitrile,
4.0% p-butylbenzoic acid p'-cyanophenyl ester,
4.0% p-pentylbenzoic acid p'-cyanophenyl ester,
5.0% p-(5-pentyl-2-pyrimidinyl)benzonitrile,
9.0% p-(5-heptyl-2-pyrimidinyl)benzonitrile,
6.0% trans-p-[5-(4-pentylcyclohexyl)-2-pyrimidinyl]-benzonitrile,
15.0% p-(trans-5-propyl-m-dioxan-2-yl)benzonitrile,
21.0% p-(trans-5-butyl-m-dioxan-2-yl)benzonitrile,
11.0% p-(trans-5-pentyl-m-dioxan-2-yl)benzonitrile,
m.p. <0°; cl.p. 63°.

EXAMPLE 15

Mixture 14+2.0 wt.% (hexylphenyl)cyclohexane, m.p. <0° C.; cl.p. 58°.

EXAMPLE 16

6.0% p-butylbenzoic acid p'-cyanophenyl ester,
14.0% p-[(p-propylbenzyliden)amino]benzonitrile,
6.0% p-(5-pentyl-2-pyrimidinyl)benzonitrile,
11.5% p-(5-heptyl-2-pyrimidinyl)benzonitrile,
5.0% 2-(4-cyanophenyl)-5-(4-butylphenyl)pyrimidine,
18.5% p-(trans-5-propyl-m-dioxan-2-yl)benzonitrile,
25.0% p-(trans-5-butyl-m-dioxan-2-yl)benzonitrile,
14.0% p-(trans-5-pentyl-m-dioxan-2-yl)benzonitrile,
   m.p. <0°; cl.p. 58°; $V_{10}$=1.05 V.

EXAMPLE 17

6.0% p-butylbenzoic acid p'-cyanophenyl ester,
14.0% p-[(p-propylbenzyliden)amino]benzonitrile,
6.0% p-(5-pentyl-2-pyrimidinyl)benzonitrile,
11.5% p-(5-heptyl-2-pyrimidinyl)benzonitrile,
6.0% trans-p-[5-(4-ethylcyclohexyl)-2-pyrimidinyl]benzonitrile,
18.5% p-(trans-5-propyl-m-dioxan-2-yl)benzonitrile,
24.0% p-(trans-5-butyl-m-dioxan-2-yl)benzonitrile,
14.0% p-(trans-5-pentyl-m-dioxan-2-yl)benzonitrile,
   m.p. <0°; cl.p. 59°; $\Delta\epsilon$=23.20; $\eta$=62 cp; $V_{10}$=1.05 V.

EXAMPLE 18

16.0% 4'-heptyl-4-cyanobiphenyl,
8.0% p-[(p-propylbenzyliden)amino]benzonitrile,
4.0% p-butylbenzoic acid p'-cyanophenyl ester,
3.5% p-pentylbenzoic acid p'-cyanophenyl ester,
4.5% p-(5-pentyl-2-pyrimidinyl)benzonitrile,
8.0% p-(5-heptyl-2-pyrimidinyl)benzonitrile,
10.0% trans-p-[5-(4-ethylcyclohexyl)-2-pyrimidinyl]benzonitrile,
15.0% p-(trans-5-propyl-m-dioxan-2-yl)benzonitrile,
20.0% p-(trans-5-butyl-m-dioxan-2-yl)benzonitrile,
11.0% p-(trans-5-pentyl-m-dioxan-2-yl)benzonitrile,
   m.p. <0°; cl.p. 62°; $\Delta\epsilon$=21.25; $\eta$=59.6 cp; $V_{10}$=1.18 V.

EXAMPLE 19

5.0% p-butylbenzoic acid p'-cyanophenyl ester,
4.5% p-pentylbenzoic acid p'-cyanophenyl ester,
5.5% p-(5-pentyl-2-pyrimidinyl)benzonitrile,
10.0% p-(5-heptyl-2-pyrimidinyl)benzonitrile,
10.0% trans-p-[5-(4-ethylcyclohexyl)-2-pyrimidinyl]benzonitrile,
17.0% p-(trans-5-propyl-m-dioxan-2-yl)benzonitrile,
24.0% p-(trans-5-butyl-m-dioxan-2-yl)benzonitrile,
13.0% p-(trans-5-pentyl-m-dioxan-2-yl)benzonitrile,
11.0% p-(trans-5-heptyl-m-dioxan-2-yl)benzonitrile,
   m.p. <−10°; cl.p. 61°; $\eta$=60.6 cp; $V_{10}$=1.13 V.

EXAMPLE 20

5.0% p-butylbenzoic acid p'-cyanophenyl ester,
5.0% p-pentylbenzoic acid p'-cyanophenyl ester,
6.0% p-(5-pentyl-2-pyrimidinyl)benzonitrile,
11.0% p-(5-heptyl-2-pyrimidinyl)benzonitrile,
6.0% trans-p-[5-(4-pentylcyclohexyl)-2-pyrimidinyl]benzonitrile,
18.0% p-(trans-5-propyl-m-dioxan-2-yl)benzonitrile,
24.0% p-(trans-5-butyl-m-dioxan-2-yl)benzonitrile,
14.0% p-(trans-5-pentyl-m-dioxan-2-yl)benzonitrile,
11.0% p-(trans-5-heptyl-m-dioxan-2-yl)benzonitrile,
   m.p. <−10°; cl.p. 58°; $\eta$=55.0 cp; $V_{10}$=1.10 V.

EXAMPLE 21

5.0% p-butylbenzoic acid p'-cyanophenyl ester,
6.0% p-(5-pentyl-2-pyrimidinyl)benzonitrile,
10.5% p-(5-heptyl-2-pyrimidinyl)benzonitrile,
19.0% trans-4-butylcyclohexane carboxylic acid p-(ethoxy)phenyl ester,
17.5% trans-4-pentylcyclohexane carboxylic acid p-(methoxy)phenyl ester,
11.0% trans-p-[5-(4-ethylcyclohexyl)-2-pyrimidinyl]benzonitrile,
17.5% p-(trans-5-propyl-m-dioxan-2-yl)benzonitrile,
13.5% p-(trans-5-pentyl-m-dioxan-2-yl)benzonitrile,
   m.p. <−10°; cl.p. 65°; $\Delta\epsilon$=14.63; $\eta$=41.6 cp; $V_{10}$=1.30 V.

EXAMPLE 22

4.5% p-butylbenzoic acid p'-cyanophenyl ester,
4.5% p-(5-pentyl-2-pyrimidinyl)benzonitrile,
8.0% p-(5-heptyl-2-pyrimidinyl)benzonitrile,
10.0% trans-4-propylcyclohexane carboxylic acid p-cyanophenyl ester,
8.0% trans-4-pentylcyclohexane carboxylic acid p-cyanophenyl ester,
15.5% trans-4-butylcyclohexane carboxylic acid p-(ethoxy)phenyl ester,
14.0% trans-4-pentylcyclohexane carboxylic acid p-(methoxy)phenyl ester,
9.0% trans-p-[5-(4-ethylcyclohexyl)-2-pyrimidinyl]benzonitrile,
15.5% p-(trans-5-propyl-m-dioxan-2-yl)benzonitrile,
11.0% p-(trans-5-pentyl-m-dioxan-2-yl)benzonitrile,
   m.p. <−10°; cl.p. 65.6°; $\eta$=41.4 cp; $V_{10}$=1.42 V.

EXAMPLE 23

4.0% p-butylbenzoic acid p'-cyanophenyl ester,
4.0% p-pentylbenzoic acid p'-cyanophenyl ester,
5.0% p-(5-pentyl-2-pyrimidinyl)benzonitrile,
9.0% p-(5-heptyl-2-pyrimidinyl)benzonitrile,
16.0% trans-4-butylcyclohexane carboxylic acid p-(ethoxy)phenyl ester,
5.0% trans-p-[5-(4-pentylcyclohexyl)-2-pyrimidinyl]benzonitrile,
15.5% p-(trans-5-propyl-m-dioxan-2-yl)benzonitrile,
21.0% p-(trans-5-butyl-m-dioxan-2-yl)benzonitrile,
11.5% p-(trans-5-pentyl-m-dioxan-2-yl)benzonitrile,
9.0% p-(trans-5-heptyl-m-dioxan-2-yl)benzonitrile,
   m.p. <−10°; cl.p. 56.5°; $\Delta\epsilon$=17.72; $\eta$=45.6 cp; $V_{10}$=1.15 V.

EXAMPLE 24

6.5% p-ethylbenzoic acid p'-cyanophenyl ester,
5.5% p-butylbenzoic acid p'-cyanophenyl ester,
5.0% p-pentylbenzoic acid p'-cyanophenyl ester,
6.0% p-(5-pentyl-2-pyrimidinyl)benzonitrile,
11.0% p-(5-heptyl-2-pyrimidinyl)benzonitrile,
10.5% trans-p-[5-(4-ethylcyclohexyl)-2-pyrimidinyl]benzonitrile,
18.0% p-(trans-5-propyl-m-dioxan-2-yl)benzonitrile,
24.0% p-(trans-5-butyl-m-dioxan-2-yl)benzonitrile,
13.5% p-(trans-5-pentyl-m-dioxan-2-yl)benzonitrile,
   m.p. <−10°; cl.p. 63.5°; $\eta$=64.8 cp; $V_{10}$=1.10 V.

EXAMPLE 25

7.5% p-ethylbenzoic acid p'-cyanophenyl ester,
6.0% p-butylbenzoic acid p'-cyanophenyl ester,
6.5% p-(5-pentyl-2-pyrimidinyl)benzonitrile,
12.0% p-(5-heptyl-2-pyrimidinyl)benzonitrile,
8.0% trans-p-[5-(4-pentylcyclohexyl)-2-pyrimidinyl]benzonitrile,
19.0% p-(trans-5-propyl-m-dioxan-2-yl)benzonitrile, 26.0% p-(trans-5-butyl-m-dioxan-2-yl)benzonitrile,
15.0% p-(trans-5-pentyl-m-dioxan-2-yl)benzonitrile,
   m.p. $<-10°$; cl.p. 62.4°; $\Delta\epsilon=23.27$; $\eta=56.5$ cp; $V_{10}=1.08$ V.

EXAMPLE 26

23.0% 4'-pentyloxy-4-cyanobiphenyl,
5.0% p-butylbenzoic acid p'-cyanophenyl ester,
6.0% p-(5-pentyl-2-pyrimidinyl)benzonitrile,
9.0% p-(5-heptyl-2-pyrimidinyl)benzonitrile,
6.5% trans-p-[5-(4-pentylcyclohexyl)-2-pyrimidinyl]benzonitrile,
16.5% p-(trans-5-propyl-m-dioxan-2-yl)benzonitrile,
21.5% p-(trans-5-butyl-m-dioxan-2-yl)benzonitrile,
12.5% p-(trans-5-pentyl-m-dioxan-2-yl)benzonitrile,
   m.p. $<-10°$; cl.p. 62.7°; $\eta=62.7$ cp; $V_{10}=1.12$ V.

EXAMPLE 27

5.0% p-butylbenzoic acid p'-cyanophenyl ester,
17.0% trans-p-(4-propylcyclohexyl)benzonitrile,
5.5% p-(5-pentyl-2-pyrimidinyl)benzonitrile,
10.0% p-(5-heptyl-2-pyrimidinyl)benzonitrile,
10.0% trans-p-[5-(4-ethylcyclohexyl)-2-pyrimidinyl]benzonitrile,
17.0% p-(trans-5-propyl-m-dioxan-2-yl)benzonitrile,
22.5% p-(trans-5-butyl-m-dioxan-2-yl)benzonitrile,
13.0% p-(trans-5-pentyl-m-dioxan-2-yl)benzonitrile,
   m.p. $<-10°$; cl.p. 58.9°; $\eta=46.2$ cp; $V_{10}=1.21$ V.

EXAMPLE 28

3.9% p-butylbenzoic acid p'-cyanophenyl ester,
3.9% p-pentylbenzoic acid p'-cyanophenyl ester,
4.9% p-(5-pentyl-2-pyrimidinyl)benzonitrile,
8.9% p-(5-heptyl-2-pyrimidinyl)benzonitrile,
15.8% trans-4-butylcyclohexane carboxylic acid p-(ethoxy)phenyl ester,
1.5% trans-p-[5-(4-ethylcyclohexyl)-2-pyrimidinyl]benzonitrile,
4.9% trans-p-[5-(4-pentylcyclohexyl)-2-pyrimidinyl]benzonitrile,
15.3% p-(trans-5-propyl-m-dioxan-2-yl)benzonitrile,
20.7% p-(trans-5-butyl-m-dioxan-2-yl)benzonitrile,
11.3% p-(trans-5-pentyl-m-dioxan-2-yl)benzonitrile,
8.9% p-(trans-5-heptyl-m-dioxan-2-yl)benzonitrile,
   m.p. $<-10°$; cl.p. 59.0°; $\Delta\epsilon=18.00$; $\eta=47.0$ cp; $V_{10}=1.15$ V.

EXAMPLE 29

4.0% p-butylbenzoic acid p'-cyanophenyl ester,
4.0% p-pentylbenzoic acid p'-cyanophenyl ester,
5.0% p-(5-pentyl-2-pyrimidinyl)benzonitrile,
8.0% p-(5-heptyl-2-pyrimidinyl)benzonitrile,
16.0% trans-4-butylcyclohexane carboxylic acid p-(ethoxy)phenyl ester,
9.0% trans-p-[5-(4-ethylcyclohexyl)-2-pyrimidinyl]benzonitrile,
15.0% p-(trans-5-propyl-m-dioxan-2-yl)benzonitrile,
19.0% p-(trans-5-butyl-m-dioxan-2-yl)benzonitrile,
11.0% p-(trans-5-pentyl-m-dioxan-2-yl)benzonitrile,
9.0% p-(trans-5-heptyl-m-dioxan-2-yl)benzonitrile,
   m.p. $<-10°$; cl.p. 60.5°; $\Delta\epsilon=18.14$; $\eta=49.3$ cp; $V_{10}=1.15$ V.

EXAMPLE 30

6.0% p-ethylbenzoic acid p'-cyanophenyl ester,
4.5% p-butylbenzoic acid p'-cyanophenyl ester,
5.0% p-(5-pentyl-2-pyrimidinyl)benzonitrile,
9.0% p-(5-heptyl-2-pyrimidinyl)benzonitrile,
16.0% trans-p-(4-propylcyclohexyl)benzonitrile,
10.5% trans-p-[5-(4-ethylcyclohexyl)-2-pyrimidinyl]benzonitrile,
16.0% p-(trans-5-propyl-m-dioxan-2-yl)benzonitrile,
21.5% p-(trans-5-butyl-m-dioxan-2-yl)benzonitrile,
11.5% p-(trans-5-pentyl-m-dioxan-2-yl)benzonitrile,
   m.p. $<-10°$; cl.p. 60.7°; $\Delta\epsilon=21,98$; $\eta=51.9$ cp; $V_{10}=1.14$ V.

EXAMPLE 31

11.0% 4'-butyl-4-cyanobiphenyl,
6.0% p-ethylbenzoic acid p'-cyanophenyl ester,
4.0% p-butylbenzoic acid p'-cyanophenyl ester,
5.0% p-(5-pentyl-2-pyrimidinyl)benzonitrile,
9.0% p-(5-heptyl-2-pyrimidinyl)benzonitrile,
12.0% trans-p-[5-(4-ethylcyclohexyl)-2-pyrimidinyl]benzonitrile,
17.0% p-(trans-5-propyl-m-dioxan-2-yl)benzonitrile,
23.0% p-(trans-5-butyl-m-dioxan-2-yl)benzonitrile,
13.0% p-(trans-5-pentyl-m-dioxan-2-yl)benzonitrile,
   m.p. $<-10°$; cl.p. 62.0°; $\Delta\epsilon=22.28$; $\eta=57.1$ cp; $V_{10}=1.13$ V.

EXAMPLE 32

7.5% p-ethylbenzoic acid p'-cyanophenyl ester,
6.0% p-butylbenzoic acid p'-cyanophenyl ester,
7.5% p-(5-pentyl-2-pyrimidinyl)benzonitrile,
14.0% p-(5-heptyl-2-pyrimidinyl)benzonitrile,
5.0% trans-p-[5-(4-pentylcyclohexyl)-2-pyrimidinyl]benzonitrile,
19.0% p-(trans-5-propyl-m-dioxan-2-yl)benzonitrile,
26.0% p-(trans-5-butyl-m-dioxan-2-yl)benzonitrile,
15.0% p-(trans-5-pentyl-m-dioxan-2-yl)benzonitrile,
   m.p. $<-10°$; cl.p. 56.8°; $\Delta\epsilon=8.75$; $\eta=59.6$ cp; $V_{10}=1.03$ V.

EXAMPLE 33

5.6% p-butylbenzoic acid p'-cyanophenyl ester,
6.6% p-hexylbenzoic acid p'-cyanophenyl ester,
6.6% p-(5-pentyl-2-pyrimidinyl)benzonitrile,
11.3% p-(5-heptyl-2-pyrimidinyl)benzonitrile,
6.0% trans-4-butylcyclohexane carboxylic acid p-(ethoxy)phenyl ester,
4.6% trans-p-[5-(4-pentylcyclohexyl)-2-pyrimidinyl]benzonitrile,
18.8% p-(trans-5-propyl-m-dioxan-2-yl)benzonitrile,
25.4% p-(trans-5-butyl-m-dioxan-2-yl)benzonitrile,
15.0% p-(trans-5-pentyl-m-dioxan-2-yl)benzonitrile,
   m.p. $<-10°$; cl.p. 55°; $\eta=44.3$ cp; $V_{10}=1.10$ V.

EXAMPLE 34

7.0% p-ethylbenzoic acid p'-cyanophenyl ester,
6.0% p-butylbenzoic acid p'-cyanophenyl ester,
10.0% p-(5-pentyl-2-pyrimidinyl)benzonitrile,
14.0% p-(5-heptyl-2-pyrimidinyl)benzonitrile,
2.0% trans-p-[5-(4-pentylcyclohexyl)-2-pyrimidinyl]benzonitrile,
20.0% p-(trans-5-propyl-m-dioxan-2-yl)benzonitrile,
26.0% p-(trans-5-butyl-m-dioxan-2-yl)benzonitrile,
15.0% p-(trans-5-pentyl-m-dioxan-2-yl)benzonitrile,
   m.p. $<-10°$; cl.p. 48°; $\eta=52.4$ cp; $V_{10}=0.93$ V.

The preparation of the compounds of formula I is illustrated by the following non-limiting Examples 35–40. All temperatures are given in degrees Centigrade. Room temperature is about 23° C. and the ether is diethyl ether. Unless otherwise stated, percentages are by weight.

EXAMPLE 35

A mixture of 11.8 g (0.1 mol) of 2-n-propylpropane-1,3-diol and 13.1 g (0.1 mol) of p-cyanobenzaldehyde in 500 ml of benzene is, after addition of 440 mg of p-toluenesulphonic acid, gassed with nitrogen and heated under reflux (bath temperature 120°) for 1 hour. The resulting water is separated with a water separator. During a further 90 minutes the benzene which condenses in the reflux condenser is then led back into the reaction vessel through a layer of 140 g of aluminium oxide. After cooling down, the mixture is stirred with 20 g of solid potassium carbonate for 1 hour, then filtered and the filtrate is freed from solvent in vacuo at 50° bath temperature. There remain behind 23.8 g of yellow oil which crystallizes upon cooling and which, according to gas chromatography, consists of 69.6% of the trans compound and 21.4% of the cis compound of p-(5-propyl-m-dioxan-2-yl)benzonitrile and 8.9% impurities. In order to obtain the pure trans compound, the mixture is recrystallized several times from hexane, ether/hexane, ether/methanol or other suitable solvents until the melting point and the clearing point remain constant and the cis compound can no longer be detected in the gas chromatogram. The pure p-(trans-5-propyl-m-dioxan-2-yl)benzonitrile forms colorless crystals and is monotropic liquid crystalline.

M.p. 57.7°–58.3°; cl.p. 43.1°; UV (ethanol) $\epsilon_{272}=960$, $\epsilon_{276}=940$.

The mother liquors (13.64 g) enriched in cis compound, which occur in the recrystallization, can be converted again into the trans-cis equilibrium mixture (65.0% trans and 18.7% cis compound) by renewed treatment with 220 mg of p-toluenesulphonic acid in 250 ml of benzene and subsequent neutralization with 10 g of potassium carbonate. Further pure trans compound is obtained by recrystallization.

EXAMPLE 36

The following compounds can be manufacture in a manner analogous to that of Example 35:
p-(Trans-5-butyl-m-dioxan-2-yl)benzonitrile, m.p. 42.7°–43.7°; cl.p. 35.6° (monotropic)
p-(trans-5-pentyl-m-dioxan-2-yl)benzonitrile, m.p. 56.2°–56.5°; cl.p. 47.9° (monotropic)
p-(trans-5-hexyl-m-dioxan-2-yl)benzonitrile, m.p. 48.2°–49.6°; cl.p. 43.5° (monotropic)
p-(trans-5-heptyl-m-dioxan-2-yl)benzonitrile, m.p. 54.0°–55.7°; cl.p. 51.5° (monotropic).

EXAMPLE 37

A solution of 10.69 g (38.55 mmol) of p-(trans-5-pentyl-m-dioxan-2-yl)benzamide in 56 ml of absolute pyridine is treated with 15.22 ml (118.6 mmol) of benzenesulphonyl chloride and left to stand closed for 16 hours at room temperature. Subsequently, the brownish reaction mixture is treated with 150 ml of 1 N sodium hydroxide and exhaustively extracted with ether. The ether solutions are washed neutral with 100 ml of 1 N sodium hydroxide and four times with 100 ml of water each time, dried over sodium sulphate and the solvent is removed in vacuo. There is obtained brownish, crystalline p-(trans-5-pentyl-m-dioxan-2-yl)benzonitrile which still contains 2.4% of the cis compound. By recrystallization from hexane, ether/hexane, ether/methanol or other suitable solvents there is obtained the pure, colorless trans compound. M.p. 56.2°–56.5°; cl.p. 47.9° (monotropic).

EXAMPLE 38

A mixture of 7.50 g (50 mmol) of p-formylbenzoic acid and 7.31 g (50 mmol) of 2-pentylpropane-1,3-diol in 250 ml of benzene is, after addition of 220 mg of p-toluenesulphonic acid, gassed with nitrogen and heated under reflux for 1 hour. Thereby, the transformation of the undissolved starting acid into the differently crystallising reaction product is clearly detectable. After treatment with aluminium oxide as in Example 35, the mixture is left to cool to room temperature. The crystals are filtered off, re-washed well with benzene and hexane and dried. 12.3 g of colorless crystals are obtained. The filtrate gives, after treatment with hexane and suction filtration, a further 1.192 g of colorless crystals. By recrystallization from dioxane there are obtained 10.7 g of colorless p-(trans-5-pentyl-m-dioxan-2-yl)benzoic acid. M.p. 210.5°–211.0°; cl.p. 211.7° (liquid crystalline).

The mother liquors enriched in cis compound, which are obtained in the recrystallization, can be converted again into the trans-cis equilibrium mixture analogously to Example 35. Further pure trans compound can be obtained by recrystallization.

EXAMPLE 39

At 0°–5° C. there is added to a solution of 10.7 g of p-(trans-5-pentyl-m-dioxan-2-yl)benzoic acid in 180 ml of absolute chloroform, after addition of 7.0 ml of triethylamine, 4.77 ml of chloroformic acid ethyl ester.

The mixture is stirred for 15 minutes at 2° and then a strong stream of ammonia gas (dried over potassium hydroxide) is conducted in for 30 minutes. Thereby, turbidity and a temperature increase immediately occur. After stirring for 3 hours at room temperature, the mixture is concentrated to dryness in vacuo, stirred for 10 minutes with 300 ml of water, the colorless suspension is filtered under suction, re-washed well with water and dried. The crude, colorless p-(trans-5-pentyl-m-dioxan-2-yl)benzamide melts at 191°–193°.

EXAMPLE 40

All p-substituted benzonitriles named in Example 40 of the present invention can be manufactured in an analogous manner to that described in Example 35.

While the invention has been described in conjunction with certain examples, it is understood that various modifications and changes may be made without departing from the spirit and scope of the invention. For example, each of compounds, V,IX and X need not always be present with compounds I, VII and VIII. The inventive mixture may only contain compounds I, V, VII and VIII or compounds I, V, VII, VIII and IX, or compounds I and VII-XI or compounds I and VII-X or compounds I, V, VII, VIII and X. If desired any of the inventive liquid crystalline mixtures may contain additional liquid crystalline compounds and/or non-liquid crystalline substances.

We claim:
1. A liquid crystalline mixture comprising:
(a) about 10 to about 75 mol percent of at least one trans-phenyl-dioxane of the formula:

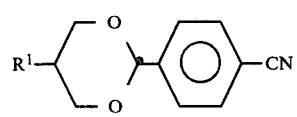

I wherein R¹ is straight chain alkyl of 3 to 7 carbon atoms;

(b) about 5 to about 30 mole percent of at least one phenylpyrimidine of the formula:

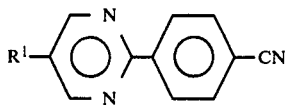
VII wherein R¹ is as above; and (c) about 2 to about 20 mol percent of at least one phenylbenzoate of the formula:

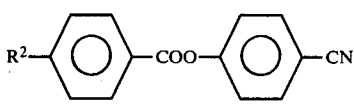
VIII wherein R² is straight chain alkyl of 2 to 7 carbon atoms.

2. The liquid crystalline mixture of claim 1 wherein R¹ of compound I is propyl, butyl or pentyl.

3. The liquid crystalline mixture of claim 1 wherein R¹ of compound VII is pentyl or heptyl.

4. The liquid crystalline mixture of claim 1 wherein R² of compound VIII is ethyl, butyl or pentyl.

5. The liquid crystalline mixture of claim 1 wherein compound I is present in the mixture in an amount of about 30 to about 70 mol percent.

6. The liquid crystalline mixture of claim 1 wherein compound VII is present in the mixture in an amount of about 10 to about 25 mol percent.

7. The liquid crystalline mixture of claim 1 wherein compound VIII is present in the mixture in an amount of from about 5 to about 17 mol percent.

8. The liquid crystalline mixture of claim 1 further comprising up to about 15 mol percent of at least one compound of the formula:

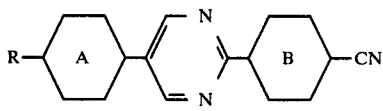
V wherein at least one of rings A and B is trans-1,4-disubstituted cyclohexane and the other is trans-1,4-disubstituted cyclohexane or aromatic, and R is straight chain alkyl of 1 to 10 carbon atoms, straight chain alkoxy of 1 to 10 carbon atoms or $C_2H_5-CH(CH_3)-(CH_2)_n-$, and n is an integer of 1 to 3.

9. The liquid crystalline mixture of claim 8 wherein compound V has the formula:

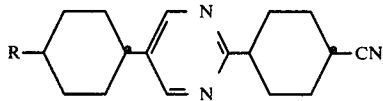
Vc

R is straight chain alkyl of 1 to 10 carbon atoms, straight chain alkoxy of 1 to 10 carbon atoms or $C_2H_5-CH(CH_3)-(CH_2)_n-$, and n is an integer of 1 to 3.

10. The liquid crystalline mixture of claim 9 wherein R is straight chain alkyl of 2 to 7 carbon atoms.

11. The liquid crystalline mixture of claim 8 wherein compound V has the formula:

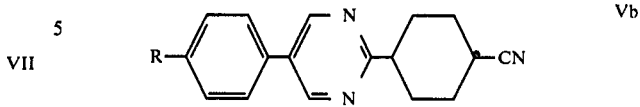
Vb

R is straight chain alkyl of 1 to 10 carbon atoms, straight chain alkoxy of 1 to 10 carbon atoms or $C_2H_5-CH(CH_3)-(CH_2)_n-$, and n is an integer of 1 to 3.

12. The liquid crystalline mixture of claim 11 wherein R is straight chain alkyl of 2 to 7 carbon atoms.

13. The liquid crystalline mixture of claim 8 wherein ring B of compound V is aromatic.

14. The liquid crystalline mixture of claim 13 wherein compound V has the formula

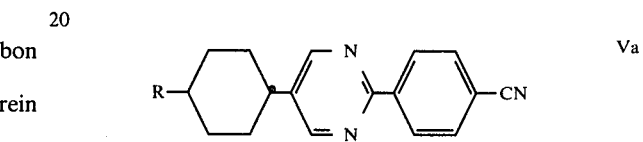
Va

R is straight chain alkyl of 1 to 10 carbon atoms, straight chain alkoxy of 1 to 10 carbon atoms or $C_2H_5-CH(CH_3)-(CH_2)_n-$, and n is an integer of 1 to 3.

15. The liquid crystalline mixture of claim 14 wherein R is straight chain alkyl of 2 to 7 carbon atoms.

16. The liquid crystalline mixture of claim 15 wherein R is ethyl, pentyl or heptyl.

17. The liquid crystalline mixture of claim 8 wherein compound V is present in the mixture in an amount of about 2 to about 10 mol percent.

18. The liquid crystalline mixture of claim 1 further comprising up to about 30 mol percent of at least one trans-cyclohexane carboxylic acid phenyl ester of the formula:

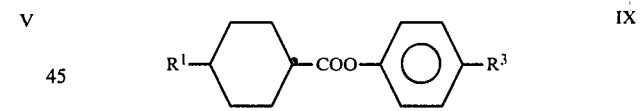
IX wherein R¹ is straight chain alkyl of 3 to 7 carbon atoms and R³ is cyano or straight chain alkoxy of 1 to 3 carbon atoms.

19. The liquid crystalline mixture of claim 18 wherein R¹ of compound IX is propyl, butyl or pentyl and R₃ is methoxy, ethoxy or propyloxy.

20. The liquid crystalline mixture of claim 19 wherein compound IX is trans-4-propylcyclohexane carboxylic acid p-cyano-phenyl ester, trans-4-butylcyclohexane carboxylic acid p-cyanophenyl ester, trans-4-pentylcyclohexane carboxylic acid p-cyanophenyl ester, trans-4-butylcyclohexane carboxylic acid p-(ethoxy)phenyl ester, trans-4-pentylcyclohexane carboxylic acid p-(methoxy)phenyl ester or trans-4-pentylcyclohexane carboxylic acid p-(propyloxy)phenyl ester.

21. The liquid crystalline mixture of claim 18 wherein compound IX is present in the mixture in an amount of about 10 to about 30 mol percent.

22. The liquid crystalline mixture of claim 1 further comprising up to about 30 mol percent of at least one Schiffs base of the formula:

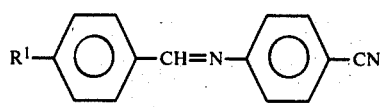

wherein $R^1$ is straight chain alkyl of 3 to 7 carbon atoms.

23. The liquid crystalline mixture of claim 22 wherein compound X is present in the mixture in an amount of about 10 to about 25 mol percent.

24. The liquid crystalline mixture of claim 22 wherein $R^1$ is propyl, butyl or hexyl.

25. The liquid crystalline mixture of claim 8 consisting of compounds I, V, VII and VIII.

26. The liquid crystalline mixture of claim 25 consisting of p-(trans-5-propyl-m-dioxan-2-yl)benzonitrile, p-(trans-5-butyl-m-dioxan-2-yl)benzonitrile, p(trans-5-pentyl-m-dioxan-2-yl)benzonitrile, p-(5-pentyl-2-pyrimidinyl)benzonitrile, p-(5-heptyl-2-pyrimidinyl)-benzonitrile, p-ethylbenzoic acid p'-cyanophenyl ester, p-butylbenzoic acid p'-cyanophenyl ester and trans-p-[5-(4-pentylcyclohexyl)-2-pyrimidinyl]benzonitrile.

27. The mixture of claim 26 consisting of about 19 mol percent p-(trans-5-propyl-m-dioxan-2-yl)benzonitrile, about 26 mol percent p-(trans-5-butyl-m-dioxan-2-yl)benzonitrile, about 15 mol percent p-(trans-5-pentyl-m-dioxan-2-yl)benzonitrile, about 6.5 mol percent p-(5-pentyl-2-pyrimidinyl)benzonitrile, about 12 mol percent p-(5-heptyl-2-pyrimidinyl)benzonitrile, about 7.5 mol percent p-ethylbenzoic acid p'-cyanophenyl ester, about 6 mol percent p-butylbenzoic acid p'-cyanophenyl ester and about 8 mol percent trans-p-[5-(4-pentylcyclohexyl)-2-pyrimidinyl]benzonitrile.

28. A liquid crystalline mixture comprising:
(a) about 10 to about 75 mol percent of a trans-phenyldioxane of the formula:

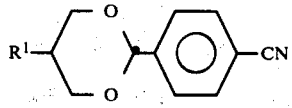

wherein $R^1$ is straight chain alkyl of 3 to 7 carbon atoms;
(b) about 5 to about 30 mol percent of a phenylpyrimidine of the formula:

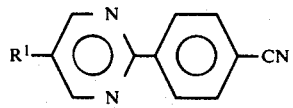

wherein $R^1$ is as above;
(c) about 2 to about 20 mol percent of a phenylbenzoate of the formula:

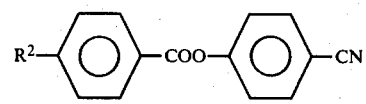

wherein $R^2$ is straight chain alkyl of 2 to 7 carbon atoms;
(d) about 0 to about 15 mol percent of a compound of the formula:

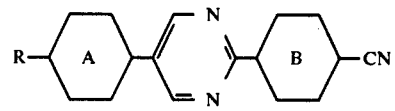

wherein at least one of rings A and B is trans-1,4-disubstituted cyclohexane and the other is trans-1,4-disubstituted cyclohexane or aromatic and R is straight chain alkyl of 1 to 10 carbon atoms, straight chain alkoxy of 1 to 10 carbon atoms or $C_2H_5-CH(CH_3)-(CH_2)_n-$, and n is an integer of 1 to 3;
(e) about 0 to about 30 mol percent of a trans-cyclohexane carboxylic acid phenyl ester of the formula:

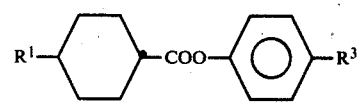

wherein $R^1$ is straight chain alkyl of 3 to 7 carbon atoms and $R^3$ is cyano or straight chain alkoxy of 1 to 3 carbon atoms; and
(f) about 0 to about 30 mol percent of a Schiffs base of the formula:

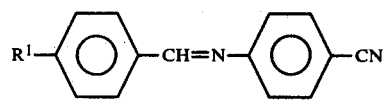

wherein $R^1$ is straight chain alkyl of 3 to 7 carbon atoms.

29. The liquid crystalline mixture of claim 28 wherein compound I is present in the mixture in about 30 to about 70 mol percent.

30. The liquid crystalline mixture of claim 28 wherein compound VII is present in the mixture in about 10 to about 25 mol percent.

31. The liquid crystalline mixture of claim 28 wherein compound VIII is present in the mixture in about 5 to about 17 mol percent.

32. The liquid crystalline mixture of claim 28 wherein compound V is present in the mixture in about 2 to about 10 mol percent.

33. The liquid crystalline mixture of claim 28 wherein compound IX is present in the mixture in about 10 to about 30 mol percent.

34. The liquid crystalline mixture of claim 28 wherein compound X is present in the mixture in about 10 to about 25 mol percent.

35. A liquid crystalline mixture comprising:
(a) about 30 to about 70 mol percent of one or more trans-phenyl-dioxanes of the formula:

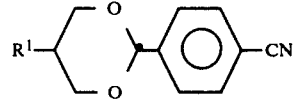

wherein $R^1$ is propyl, butyl or pentyl;
(b) about 10 to about 25 mol percent of one or more phenylpyrimidines of the formula:

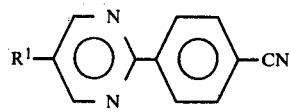

wherein R¹ is pentyl or heptyl;

(c) about 5 to about 17 mol percent of one or more phenylbenzoates of the formula:

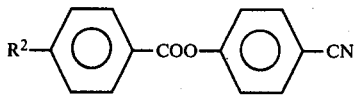

wherein R₂ is ethyl, butyl or pentyl;

(d) about 2 to about 10 mol percent of one or more compounds of the formula:

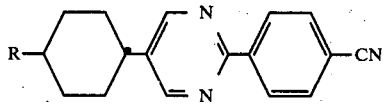

wherein R is ethyl, pentyl or heptyl;

(e) about 10 to about 30 mol percent of one or more trans-cyclohexane carboxylic acid phenyl esters of the formula:

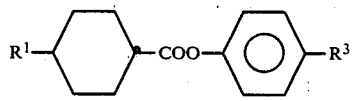

wherein R¹ is propyl, butyl or pentyl and R₃ is cyano, methoxy, ethoxy or propyloxy; and (f) about 10 to about 25 percent of one or more Schiffs bases of the formula:

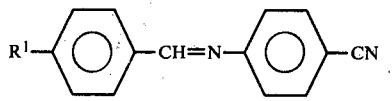

wherein R¹ is propyl, butyl or hexyl.

36. In an electro-optical liquid crystal display containing a liquid crystalline mixture having positive dielectric anisotrophy, the improvement wherein the liquid crystalline mixture comprises:

(a) about 10 to about 75 mol percent of a trans-phenyl-dioxane of the formula:

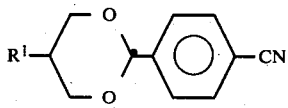

wherein R¹ is straight-chain alkyl of 3 to 7 carbon atoms;

(b) about 5 to about 30 mol percent of a phenyl-pyrimidine of the formula:

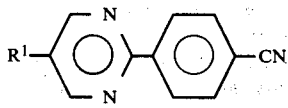

wherein R¹ is as above; and (c) about 2 to about 20 mol percent of a phenylbenzoate of the formula:

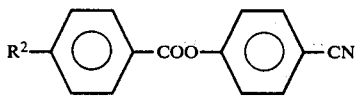

wherein R² is straight-chain alkyl of 2 to 7 carbon atoms.

37. A twisted-nematic, rotational electro-optic display improved as per claim 36.

* * * * *